(12) United States Patent
Cornelius et al.

(10) Patent No.: US 7,129,273 B2
(45) Date of Patent: Oct. 31, 2006

(54) DICREATINE MALATE

(75) Inventors: Derek Wayne Cornelius, Cape Girardeau, MO (US); Gary Lee Haynes, Scott City, MO (US)

(73) Assignee: Creative Compounds, LLC, Scott City, MO (US)

( * ) Notice: Subject to any disclaimer, the term of this patent is extended or adjusted under 35 U.S.C. 154(b) by 110 days.

(21) Appl. No.: 10/249,683

(22) Filed: Apr. 30, 2003

(65) Prior Publication Data

US 2004/0220263 A1    Nov. 4, 2004

(51) Int. Cl.
*A61K 31/20*    (2006.01)
*C07C 251/00*    (2006.01)
(52) U.S. Cl. .................. 514/564; 562/560
(58) Field of Classification Search ........... 562/60, 562/560
See application file for complete search history.

(56) References Cited

U.S. PATENT DOCUMENTS

2002/0150627 A1 * 10/2002 Stout et al. ............. 424/601

* cited by examiner

*Primary Examiner*—Paul A. Zucker

(57) ABSTRACT

This invention relates to a novel compound, dicreatine malate, comprising approximately two moles of creatine cations per one mole of malate anion. The creatine salt of this invention has been found to increase the bioavailability of both the creatine and malic acid moieties over and above the individual bioavailabilities of creatine monohydrate and malic acid base. Dicreatine malate vastly improves the production of Adenosine TriPhosphate (ATP) beyond the level of creatine monohydrate or any other creatine derivative. It also has a much greater efficacy in uses such as increasing muscle mass, increasing cell volumization, decreasing adipose stores, and for increasing overall strength and endurance.

10 Claims, No Drawings

DICREATINE MALATE

BACKGROUND OF INVENTION

Reference Cited [Referenced by]
U.S. Patent Documents:
U.S. Pat. No. 6,211,407 April, 2001 Thomson 562/560
U.S. Pat. No. 5,863,939 January, 1999 Pischel, et al. 514/474
U.S. Pat. No. 5,886,040 March, 1999 Fang 514/557
U.S. Pat. No. 5,973,199 October, 1999 Negrisoli, et al. 562/560

Other References:
G. E. Abraham and J. D. Flechas, Journal of Nutritional Medicine 1992; 3: 49–59.
V. V. Dunaev, et al., "Effect of Malic Acid Salts on Physical Work Capacity and its Recovery after Exhausting Muscular Activity," Famakol Toksikol 51(3) (1988): 1–25.
V. Bobyleva-Guarriero, et al., "The Role of Malate in Exercise-induced Enhancement of Mitochondrial Espiration," Arch Biochem Biophys 245(2) (19086): 470–76.
Le Boucher J, Cynober LA. "Ornithine alpha-ketoglutarate: the puzzle." Nutrition 1998; 14: 8703 [review].
Jeevanandam M, et al., "Ornithine-alpha-Ketogluterate (OKG) Supplementation is more effective than its component salts in traumatized rats." J. Nutr. 1996 September; 126(9): 2141–50.

DETAILED DESCRIPTION

The present invention refers to a novel compound, dicreatine malate, its uses and biological effects. Since prior art gives no clue, the inventors were taken by surprise by the extraordinary properties and effects of dicreatine malate. Combining approximately two cations of creatine with one malic acid dianion into a single compound has shown to be much more effective and more readily absorbed than any other form of creatine or malic acid supplement currently available.

Dicreatine malate presents unique and useful synergistic attributes due to the combination of the malic acid and creatine. Both malic acid and creatine are essential in the production of Adenosine TriPhosphate (ATP). Either of these chemical entities are useful in the production of high energy phosphate molecules such as ATP. It would be expected that a 2:1 combination of creatine and malic acid would produce an additive effect at most on the production of these high energy phosphate molecules. However, although we are not certain of the exact reason, combining these two chemical entities in approximately a 2:1 ratio gives a compound that increases the production of ATP to a much greater extent than what would be expected by the mere additive effects of creatine and malic acid taken separately. It is now obvious to the inventors that some type of synergism is taking place between the creatine and malic acid when combined as dicreatine malate.

At first glance, this seemed impossible to the inventors as the effect should have definitely been additive. However, upon reviewing the literature, it was found that other ionic compounds have been also shown to display this unexpected synergism. For example, ornithine alpha-ketoglutarate has been shown to produce a strong anti-catabolic effect on burn victims far greater in effect than what is produced by merely combining the effects of the molar equivalents of ornithine base and alpha-ketoglutaric acid taken separately.

Creatine, also known as N-(Aminoiminomethyl)—N-methylglycine is a naturally occurring metabolite found in red muscle tissue. Creatine phosphate (also known as phosphocreatine) helps provide ATP during short bursts of high intensity exercise and has been associated with the onset of fatigue when there is a depletion of phosphocreatine.

Creatine is synthesized from amino acids in the liver, pancreas, and kidney, by the transfer of the guanidine moiety of arginine to glycine, which is then methylated to form creatine. It is then released into the bloodstream and actively taken up by the muscle cells.

Due to the body's inability to produce adequate amounts of creatine and phosphocreatine (and thus ATP), especially during times of high intensity activities, oral supplementation is needed. The dicreatine malate of this invention has been shown to be an ideal method of supplementing the body efficiently with an adequate amount of creatine, phosphocreatine and ATP.

Malic acid, a naturally occurring compound found in a wide variety of fruits and vegetables, is also present in all living cells and is essential in the production of ATP. Malic acid sparks the Krebs cycle and is the only metabolite of the cycle which falls in concentration during exhaustive physical activity. Depletion of malic acid has been linked to physical exhaustion. Malic acid supports the removal of compounds that build up under hypoxic conditions and inhibit ATP production. Malic acid is also a potent aluminum detoxifier and is effective in decreasing aluminum toxicity in various organs and tissues including the brain. It has also been show to aid in reducing muscle pain and increasing endurance.

U.S. Pat. No. 5,973,199 discloses a monocreatine malate, but does not have any disclosure for dicreatine malate. U.S. Pat. No. 5,973,199 only refers to the combination of one mole of creatine monohydrate with one mole of malic acid (monocreatine malate). Dicreatine malate requires approximately a two-to-one molar ratio of creatine to malic acid. U.S. Pat. No. 5,973,199 makes no mention of the superior combination of two creatine molecules with one malic acid molecule. Our experience shows that indeed the 1:1 molar ratio salt is inferior to the dicreatine malate of this invention.

U.S. Pat. No. 6,211,407 discloses di- and tri-creatine salts of citric acid, but makes no mention of any other dicreatine salts such as dicreatine malate. Furthermore, this patent makes no mention of any superiority in terms of enhanced metabolic effects such as vastly increased ATP production. In fact, the inventors have found that although the citric acid is a Krebs cycle intermediate, when combined with creatine in a 1:2 or 1:3 ratio it does not have the vastly improved effect of dicreatine malate.

Human dosaging for Dicreatine malate is in the range of about 1 mg/kg to 1 g/kg of bodyweight per day, and most preferable in the range of 20–220 mg/kg of bodyweight per day. Although the Dicreatine malate of this invention can be dosed once per day for a desired effect, we have found that it is best to divide the dosage into two or three equal amounts given eight to twelve hours apart. This helps to ensure steady blood values and an overall more powerful, consistent effect. Effective dosaging may be in the form of tablets, hard and soft gelatin capsules, sachets, effervescent powder or tablets, liquid or other oral delivery system known in the art.

The inventors have also found that this form of creatine gives added benefit by decreasing some of the problems associated with other creatine supplementation, such as cramping, bloating, and bioavailability issues. Further, Dicreatine malate has shown enhanced metabolic properties compared to creatine monohydrate, for example, enhanced efficacy for increasing muscle mass, enhanced efficacy for increasing cell volumization, enhanced efficacy for decreasing adipose stores, enhanced efficacy for increasing for increasing overall strength and endurance. Still further, Dicreatine malate has been shown to increase the bioavailablities of both the creatine and malic acid moieties over the individual bioavailabilities of creatine monohydrate and malic acid.

The invention claimed is:

1. A dicreatine malate compound comprising approximately two creatine cations per one malic acid dianion.

2. A dicreatine malate compound in accordance with claim 1 comprising a creatine content of about 66 percent by weight and a malic acid content of about 33 percent by weight.

3. A dicreatine malate compound in accordance with claim 1 in the form selected from the group consisting of tablets, hard gelatin capsules, soft gelatin capsules, sachets, a powder, an effervescent powder, and a liquid.

4. A method of increasing the production of adenosine triphosphate in a human body comprising administering to a subject a dicreatine malate compound comprising approximately two creatine cations per one malic acid dianion.

5. A method in accordance with claim 4 wherein the dicreatine malate compound comprises a creatine content of about 66 percent by weight and a malic acid content of about 33 percent by weight.

6. A method in accordance with claim 4 wherein said administering to a subject a dicreatine malate compound comprises administering to a subject a dicreatine malate compound in a daily dosage of about 1mg/kg of bodyweight to about 1 g/kg of bodyweight.

7. A method in accordance with claim 6 wherein said administering to a subject a dicreatine malate compound comprises administering to a subject a dicreatine malate compound in a daily dosage of about 20mg/kg of bodyweight to about 220 mg/kg of bodyweight.

8. A method in accordance with claim 4 wherein said administering to a subject a dicreatine malate compound comprises administering to a subject a dicreatine malate compound in a daily dosage of about 1mg/kg of bodyweight to about 1 g/kg of bodyweight in two equal amounts given twelve hours apart.

9. A method in accordance with claim 4 wherein said administering to a subject a dicreatine malate compound comprises administering to a subject a dicreatine malate compound in a daily dosage of about 1mg/kg of bodyweight to about 1 g/kg of bodyweight in three equal amounts given eight hours apart.

10. A method in accordance with claim 4 wherein said administering to a subject a dicreatine malate compound comprises administering to a subject a dicreatine malate compound in the form selected from the group consisting of tablets, hard gelatin capsules, soft gelatin capsules, sachets, a powder, an effervescent powder, and a liquid.

* * * * *